(12) United States Patent
Chubb

(10) Patent No.: US 6,452,188 B1
(45) Date of Patent: Sep. 17, 2002

(54) SPECTRAL REFLECTANCE SCALE METHOD AND APPARATUS

(76) Inventor: Charles R. Chubb, P.O. Box 1445, St. Charles, MO (US) 63302-1445

( * ) Notice: Subject to any disclaimer, the term of this patent is extended or adjusted under 35 U.S.C. 154(b) by 0 days.

(21) Appl. No.: 09/382,768

(22) Filed: Aug. 25, 1999

(51) Int. Cl.[7] .................................................. G01J 1/00
(52) U.S. Cl. .................. 250/372; 250/338.1; 250/461.2
(58) Field of Search ............................. 250/372, 338.1, 250/461.2

(56) References Cited

U.S. PATENT DOCUMENTS

| | | | | |
|---|---|---|---|---|
| 4,882,598 A | * | 11/1989 | Wulf | 250/338.1 |
| 5,365,068 A | * | 11/1994 | Dickerson | 250/372 |

* cited by examiner

Primary Examiner—Constantine Hannaher
Assistant Examiner—Andrew Israel
(74) Attorney, Agent, or Firm—Henry W. cummings

(57) ABSTRACT

Methods and apparatus for measuring the reflectance in a visible spectral wavelength band by visual comparison of a surface viewed through a filter with a set of reference reflectance areas are described. An appropriate filter and reference reflecting areas are useful for estimating skin pigmentation, corresponding skin sun sensivity and sun exposure time tolerance. Tables are included for the solar erythemal radiation environment in different locations for different times of the year for use in determining sunlight exposure time tolerance. Also methods to use skin reflectance data along with local solar ultraviolet index data to determine sunlight exposure tolerance times are included. In addition, methods to ensure sufficient exposure for previtamin D generation are included along with techniques to reduce the risk of skin cancer. The combination of a filter and gray scale for the reflectance measurement results in a low cost device in comparison with other meters and instruments making the device affordable for many persons.

8 Claims, 14 Drawing Sheets

TABLE I

SKIN DAMAGE AND MINIMUM EXPOSURE TIMES

SKIN TYPE II, UNTANNED, 21 MJ/SQ CM

| SOLAR UV INDEX | DAMAGE TIME MINUTES | MINIMUM (0.15 MED) MINUTES |
|---|---|---|
| 1 | 140 | 21 |
| 2 | 70 | 11 |
| 3 | 47 | 7 |
| 4 | 35 | 5 |
| 5 | 28 | 4 |
| 6 | 23 | 4 |
| 7 | 20 | 3 |
| 8 | 18 | 3 |
| 9 | 16 | 2 |
| 10 | 14 | 2 |
| 11 | 13 | 2 |
| 12 | 12 | 2 |

FIG. 6

TABLE II

GRAY SCALE PARAMETERS

| PATCH | REFLECTIVITY PERCENTAGE | PRECALIBRATION EXAMPLE MED MJ/SQCM |
|:-:|:-:|:-:|
| 1 | 89 | 10 |
| 2 | 71 | 20 |
| 3 | 56 | 40 |
| 4 | 45 | 60 |
| 5 | 35 | 80 |
| 6 | 28 | 100 |
| 7 | 22 | 120 |
| 8 | 18 | 140 |
| 9 | 14 | 160 |
| 10 | 11 | 180 |
| 11 | 9 | 200 |
| 12 | 7 | 220 |

FIG. 7

TABLE III

SKIN DAMAGE TIME, MINUTES, FROM UV INDEX AND MED

| MED MJ/SQ CM | \ UV INDEX | | | | | | | | | | |
|---|---|---|---|---|---|---|---|---|---|---|---|
| | 1 | 2 | 3 | 4 | 5 | 6 | 7 | 8 | 9 | 10 | 11 |
| 10 | 67 | 33 | 22 | 17 | 13 | 11 | 10 | 8 | 7 | 7 | 6 |
| 20 | 133 | 67 | 44 | 33 | 27 | 22 | 19 | 17 | 15 | 13 | 12 |
| 40 | | 133 | 89 | 67 | 53 | 44 | 38 | 33 | 30 | 27 | 24 |
| 80 | | | | 133 | 107 | 89 | 76 | 67 | 59 | 53 | 48 |
| 160 | | | | | | | | 133 | 119 | 107 | 97 |

FIG. 8

TABLE IIIa
BRIGHT DAY SKIN DAMAGE TIME, MINUTES, MOBILE ALABAMA

| GRAY SCALE PATCH | PRECAL MED $mJ/cm^2$ | APR | MAY | JUN | JUL | AUG | SEP |
|---|---|---|---|---|---|---|---|
| 1 | 10 | 7 | 7 | 7 | 7 | 7 | 8 |
| 2 | 20 | 15 | 13 | 13 | 13 | 15 | 17 |
| 3 | 40 | 30 | 27 | 27 | 27 | 30 | 33 |
| 4 | 60 | 44 | 40 | 40 | 40 | 44 | 50 |
| 5 | 80 | 59 | 53 | 53 | 53 | 59 | 67 |
| 6 | 100 | 74 | 67 | 67 | 67 | 74 | 83 |
| 7 | 120 | 89 | 80 | 80 | 80 | 89 | 100 |
| 8 | 140 | 104 | 93 | 93 | 93 | 104 | 117 |
| 9 | 160 | 119 | 107 | 107 | 107 | 119 | |
| 10 | 180 | * | 120 | 120 | 120 | | |
| 11 | 200 | | | | | | |
| 12 | 220 | | | | | | |

| GRAY SCALE PATCH | PRECAL MED $mJ/cm^2$ | JAN | FEB | MAR | OCT | NOV | DEC |
|---|---|---|---|---|---|---|---|
| 1 | 10 | 13 | 11 | 8 | 10 | 17 | 22 |
| 2 | 20 | 27 | 22 | 17 | 19 | 33 | 44 |
| 3 | 40 | 53 | 44 | 33 | 38 | 67 | 89 |
| 4 | 60 | 80 | 67 | 50 | 57 | 100 | |
| 5 | 80 | 107 | 89 | 67 | 76 | | |
| 6 | 100 | * | 111 | 83 | 95 | | |
| 7 | 120 | | | 100 | 114 | | |
| 8 | 140 | | | 117 | | | |
| 9 | 160 | | | | | | |
| 10 | 180 | | | | | | |
| 11 | 200 | | | | | | |
| 12 | 220 | | | | | | |

\* BLANK VALUES: GREATER THAN 120 MINUTES

FIG. 8a

TABLE IV

SKIN DAMAGE TIME, MINUTES, FOR CLEAR DAY

MINIMUM ERYTHEMAL DOSE: 20 MJ/CM$^2$

| Latitude degrees | JAN | FEB | MAR | APR | MAY | JUNE | JULY | AUG | SEPT | OCT | NOV | DEC |
|---|---|---|---|---|---|---|---|---|---|---|---|---|
| 0  | 15  | 13  | 13  | 15 | 16  | 16 | 16 | 14 | 12  | 13 | 15  | 15  |
| 5  | 16  | 14  | 14  | 14 | 16  | 16 | 15 | 14 | 13  | 15 | 16  | 16  |
| 10 | 16  | 15  | 15  | 13 | 15  | 15 | 14 | 13 | 14  | 16 | 17  | 19  |
| 15 | 22  | 17  | 17  | 15 | 15  | 15 | 14 | 14 | 15  | 17 | 22  | 25  |
| 20 | 26  | 18  | 17  | 16 | 14  | 14 | 13 | 15 | 16  | 18 | 26  | 30  |
| 25 | 35  | 25  | 20  | 18 | 16  | 15 | 15 | 17 | 17  | 23 | 33  | 40  |
| 30 | 42  | 30  | 21  | 19 | 17  | 16 | 16 | 18 | 18  | 28 | 39  | 60  |
| 35 | 79  | 42  | 29  | 23 | 21  | 18 | 18 | 20 | 23  | 36 | 67  | 108 |
| 40 | 119 | 55  | 36  | 24 | 22  | 19 | 19 | 21 | 28  | 46 | 101 |     |
| 45 |     | 101 | 51  | 32 | 26  | 21 | 22 | 26 | 36  | 79 |     |     |
| 50 |     |     | 62  | 39 | 28  | 22 | 23 | 32 | 43  | 119|     |     |
| 55 |     |     | 101 | 51 | 36  | 26 | 29 | 41 | 69  |    |     |     |
| 60 |     |     |     | 63 | 44  | 32 | 36 | 50 | 108 |    |     |     |
| 65 |     |     |     | 95 | 56  | 39 | 44 | 79 |     |    |     |     |
| 70 |     |     |     |    | 69  | 48 | 54 | 115|     |    |     |     |
| 75 |     |     |     |    | 111 | 63 | 85 |    |     |    |     |     |
| 80 |     |     |     |    |     | 101|    |    |     |    |     |     |

FIG. 9

TABLE V

AVERAGE DAILY ERYTHEMAL EXPOSURE, MED'S OFFICE WORKERS, CLEAR DAYS

| MED MJ/CM$^2$ | LATITUDE DEGREES | NOV | DEC | JAN | JUN | JUL | AUG |
|---|---|---|---|---|---|---|---|
| 20 | 0 | 1.37 | 1.37 | 1.50 | 1.22 | 1.31 | 1.40 |
| 20 | 10 | 1.07 | 1.08 | 1.22 | 1.37 | 1.40 | 1.43 |
| 20 | 20 | 0.75 | 0.75 | 0.75 | 1.41 | 1.40 | 1.35 |
| 20 | 30 | 0.44 | 0.42 | 0.53 | 1.38 | 1.35 | 1.19 |
| 20 | 40 | 0.20 | 0.17 | 0.23 | 1.22 | 1.16 | 0.92 |
| 20 | 50 | 0.09 | 0.06 | 0.11 | 1.02 | 0.92 | 0.68 |
| 40 | 0 | 0.68 | 0.68 | 0.75 | 0.61 | 0.65 | 0.70 |
| 40 | 10 | 0.53 | 0.54 | 0.61 | 0.68 | 0.70 | 0.71 |
| 40 | 20 | 0.38 | 0.38 | 0.38 | 0.71 | 0.70 | 0.68 |
| 40 | 30 | 0.22 | 0.21 | 0.26 | 0.69 | 0.68 | 0.59 |
| 40 | 40 | 0.10 | 0.08 | 0.11 | 0.61 | 0.58 | 0.46 |
| 40 | 50 | 0.05 | 0.03 | 0.05 | 0.51 | 0.46 | 0.34 |
| 80 | 0 | 0.34 | 0.34 | 0.38 | 0.30 | 0.33 | 0.35 |
| 80 | 10 | 0.27 | 0.27 | 0.30 | 0.34 | 0.35 | 0.36 |
| 80 | 20 | 0.19 | 0.19 | 0.19 | 0.35 | 0.35 | 0.34 |
| 80 | 30 | 0.11 | 0.11 | 0.13 | 0.35 | 0.34 | 0.30 |
| 80 | 40 | 0.05 | 0.04 | 0.06 | 0.30 | 0.29 | 0.23 |
| 80 | 50 | 0.02 | 0.02 | 0.03 | 0.26 | 0.23 | 0.17 |
| 160 | 0 | 0.17 | 0.17 | 0.19 | 0.15 | 0.16 | 0.17 |
| 160 | 10 | 0.13 | 0.14 | 0.15 | 0.17 | 0.17 | 0.18 |
| 160 | 20 | 0.09 | 0.09 | 0.09 | 0.18 | 0.17 | 0.17 |
| 160 | 30 | 0.05 | 0.05 | 0.07 | 0.17 | 0.17 | 0.15 |
| 160 | 40 | 0.02 | 0.02 | 0.03 | 0.15 | 0.14 | 0.11 |
| 160 | 50 | 0.01 | 0.01 | 0.01 | 0.13 | 0.11 | 0.08 |

FIG. 10

TABLE VI

DARK SKIN OFFICE WORKER AVERAGE DAILY EXPOSURE, MED's

| LATITUDE DEGREES | JANUARY | OCTOBER |
|---|---|---|
| 0 | 0.20 | 0.22 |
| 5 | 0.18 | 0.20 |
| 10 | 0.17 | 0.19 |
| 15 | 0.15 | 0.18 |
| 20 | 0.12 | 0.16 |
| 25 | 0.09 | 0.14 |
| 30 | 0.06 | 0.12 |
| 35 | 0.04 | 0.09 |
| 40 | 0.02 | 0.07 |
| 45 | 0.01 | 0.05 |
| 50 | 0.01 | 0.03 |
| 55 | 0.00 | 0.02 |
| 60 | 0.00 | 0.01 |

\* CALCULATED USING ENVIRONMENTAL MODEL WITH CLOUDS

PHOTOCHEM. PHOTOBIO. 69:193-202;1999

OFFICER WORKER MED: 80 MJ/CM$^2$

EXPOSURE: 3% OF AMBIENT

FIG. 11

SPECTRAL REFLECTANCE SCALE METHOD AND APPARATUS

BACKGROUND OF THE INVENTION

Migration has resulted in large populations living in areas with sunlight environments not suited to their skin type. Migration toward the equator has resulted in light skin persons with difficulty in avoiding overexposure with sunburns and increased risk of skin cancer. Migration away from the equatorial regions has resulted in dark skin persons with difficulty in getting enough sunlight exposure in the wintertime to avoid vitamin D deficiency and associated health problems. Many light skin persons and especially older persons also incur problems with vitamin D deficiency.

One specific problem is the difficulty in knowing how long an individual can be exposed to outdoor sunlight without having a later development of red skin or a painful burn. The problem is particularly severe for young children who have not developed a general knowledge of their tolerance to sunlight in the spring and early summer. Public surveys of the response to the ultraviolet index predictions of the National Weather Service have resulted in a desire for further information such as burn time, Geller. Skin damage time, a term often used rather than burn time, varies so greatly from individual to individual that skin damage time data for a reference skin type is of very limited usefulness.

A second problem is knowing how long an individual needs to be exposed to sunlight for good health. There are many beneficial effects of sunlight exposure. The Health Council of the Netherlands estimated the yearly minimum dose to be 55 MED for an average of 0.15 MED per day, World Health Organization EHC-160, page 131. Avoidance of reddened skin at a dose of 1 MED leaves a relatively small ratio of sunburn dose to minimum dose of slightly less than 7 to 1 (1/0.15).

In addition to just avoiding skin reddening, many high ultraviolet radiation doses greatly increase the risk of skin cancer. Tests with hairless mice at an ultraviolet irradiance of about 0.7 MED 5 days/week for 11 weeks lead to 90% of animals with tumors by week 34, Black 1995. Many persons avoid sunlight to reduce the risk of skin cancer, however too little ultraviolet radiation can result in insufficient vitamin D which is believed to increase the risk of cancer, Garland and risk of high blood pressure, heart disease and other conditions of decreased health, Kime.

The limits for too much and too little ultraviolet erythemal radiation vary from individual to individual depending on factors including the darkness of the skin, age, diet, and other conditions affecting tolerance to ultraviolet radiation exposure. The exposure of a dark skin individual necessary to produce vitamin D levels sufficient to reduce the risk of cancer (as estimated by Garland) can be greater than six times the exposure needed by a light skin individual, Holick 1985. Age is a significant factor in the formation of previtamin D in the skin by sunlight. Skin samples of 8 and 18 year old subjects produced two to three times as much previtamin D as skin samples of 77 and 82 year old subjects when exposed to simulated solar radiation, Chen. Older persons do not produce as much circulating 25-OH vitamin D as young persons when exposed to whole body irradiation by ultraviolet light, Chen. Most of the skin areas gradually darken with age, Lock-Anderson, making it increasingly difficult to obtain sufficient sunlight exposure for vitamin D formation at older ages during the winter.

During the spring and summer light skin persons are often susceptible to overexposure. Avoidance of exposure for long periods outdoors or use of sunscreen lotion, protective clothing and a broad brim hat are wise choices for an individual under this condition, Long. The development of a tan can increase the MED and corresponding outdoor exposure tolerance with longer burn time, Fitzpatrick 1972, p755. The term burn associated with sunburn is histologically different than a thermal burn, however, many of the clinical symptoms are similar, Urbach.

Daily doses much less than one MED over long periods of time are desirable to maintain a low risk of skin cancer. As shown by Blum in tests with animals, carcinogenesis is closely dose dependent for moderate and high dose rates. However, for low dose rates, carcinogenesis is greatly reduced. Low ultraviolet dose rates such as 0.15 MED are desirable to reduce the risk of skin cancer. The body can repair much of the DNA damage due to many factors including the presence of free radicals and exposure to ultraviolet radiation, Shigenaga. Low daily ultraviolet radiation doses rates are necessary so the number of damage sites will be within the daily repair capability of the body as limited by other factors such as diet.

An estimate of the dose that corresponds to one MED for an individual is sometimes based on the sunburn tendency such as always, usually, sometimes or rarely. However, this results in wide range estimates subject to large error. An improved technique is desirable.

Solar Radiation Enviroment

The solar radiation environment is predicted daily by the National Weather Service and it can be measured by commercial cards and meters. Also environmental models predict the average environment by time of the year and location.

Solar radiation ultraviolet index (UVI) daily predictions to aid in avoiding solar ultraviolet radiation overexposure now available from the National Weather Service have been criticized since individuals cannot easily determine how long they can be exposed outdoors on bright spring and summer days without getting a sunburn, Geller. The ultraviolet index unit corresponds to 25 milliwatts/square meter for the erythemally weighted dose rate unit, Long. This factor along with the UVI, and an individual's MED (typical units: $mJ/cm^2$) enable the calculation of the burn time. The primary problem is the estimation of an individual's MED. In addition to the problem of determining the burn time for light skin individuals, a method for determining the time for sufficient light exposure for dark skinned individuals is not generally available and utilized.

In Philadelphia, the Solar Light Company maintains a website with daily values of the minimum erythemal dose (MED) for half hour periods for a type II individual. Erythemal refers to reddening. Skin damage times can be evaluated for an average type II individual using this type of data or National Weather Service UVI data to avoid excessive daily sun exposure. As an example on Jul. 18, 1998 at 12:00 the dose rate in Philadelphia was 1.7 MED's per half hour period. The skin damage time for 1 MED was 30 minutes/1.7 which is just under 18 minutes for a type II individual having an MED of 21 $mJ/cm^2$.

In using the daily solar radiation ultraviolet data one problem is how do individuals determine their sensitivity ratio relative to an average type II individual or their sensitivity (MED). The relative sensitivity or MED is necessary so they can estimate their own or their children's safe exposure time and avoid sunburns yet obtain sufficient light necessary for beneficial effects.

In addition to the daily solar radiation predictions by the National Weather Service and the Solar Light Company daily reports, two models predict the average solar radiation environment for the different times of the year. Madronich evaluated the daily solar radiation for clear days for different months at different latitudes. The values can be used to estimate the average daily erythemal exposure for clear days. A model of global ultraviolet radiation including local atmospheric conditions and surface elevation was generated by Sabziparvar. The values can be used to estimate the average daily erythemal exposure including the effects of clouds rather than just for clear days. The clear day values of Madronich's model are useful for determining exposure limits for avoidance of overexposure on clear days. The values of Sabziparvar's model for average days including effects of clouds is useful for determining the necessary exposure to avoid underexposure and possible vitamin D deficiency problems.

Individuals living at high elevations experience increased erythemal ultraviolet exposure in comparison to individuals living at lower elevations. The ultraviolet radiation environment is increased at higher elevations due to the shorter path length through the atmosphere for solar radiation and the relatively high attenuation of the atmosphere for ultraviolet radiation. The decrease in skin damage time with increase in altitude is about 6%/kilometer or greater, Long.

Commercial exposure cards are available for determining when the accumulated exposure is close to the sunburn level. However, their effectiveness in determining when an individual using sunscreen should come in out of the sunlight has been questioned, Mosley. As shown by animal tests many daily exposures at levels that do not cause skin reddening result in skin cancer. Thus a time that is short enough for avoiding sunburn for a single day is not safe for avoiding skin cancer if there are too many days of exposure close to the limit for sunburn. A daily exposure near 0.15 MED appears to be sufficient for vitamin D generation and other functions while many exposures near 1 MED or greater increase the risk of skin cancer.

Individual Exposure to the Solar Radiation Environment

Leach found office workers have an exposure of about 3% of the ambient clear day environmental erythemal radiation while outdoor workers have an exposure of about 10% of the erythemal ambient environment.

These percentage exposures along with the environmental characteristics enable the average exposure of individuals in different areas to be estimated for different times of the year in units such as the daily erythemal exposure in $mJ/cm^2$. The next question is: what is the minimum erythemal dose in $mJ/cm^2$ for individuals with different types of skin?

Skin Erythema Measurements

An individual's sun sensitivity can be determined by exposure to a lamp ultraviolet source and observation of the skin for reddening at later times such as 8 and 24 hours after exposure. This technique is normally restricted to research studies and for phototherapy patients due to necessity for delayed observations, the expense and the undesirability of even small burns or reddening of the skin. The measurements are very sensitive to the spectral distribution of the light source. Several spectral weighting factors including the CIE, IRPA/INIRC (WHO EHC-160 p61) and various action spectra are used to evaluate the erythemal exposure. The measurements are also greatly affected by the subjective judgment of minimum reddening by different observers. Thus relative MED's within single investigations provide better comparisons than MED's reported by different investigators due to the different evaluation techniques.

Individual Variations in Sun Sensitivity

Sun sensitivity varies with several factors. First, sun sensitivity varies greatly with the darkness of the skin. Individuals with light colored skin tend to have the greatest sensitivity with short burn times for bright summer days. Very dark skinned individuals tend to have long burn times or are able to tolerate outdoor sunlight for the entire day without developing a sunburn. However, light skin individuals have an advantage in the winter since they need much less light to form previtamin D than dark skin individuals. Second, sun sensitivity varies for different parts of the skin for each individual. The normally uncovered face and back of the hands tend to develop a protective tan while areas normally covered by clothing or bathing suits tend to be the lightest color and the most sensitive to sun exposure. Third, sun sensitivity changes with time and age due to several factors. Normally unexposed skin such as buttock skin gets lighter from birth to about age 25 for whites and then doesn't change greatly for older ages while other areas tend to get darker at a nearly uniform rate throughout the lifetime, Lock-Anderson. Tanning in the spring makes one less sensitive to sun exposure, however for individuals with types II and III skin the protection is modest (of the order of a factor of two), Sheehan. Diet, medication and exposure to chemicals and substances in the environment also can affect the sensitivity to sunlight. Also, sun sensitivity varies with diet. A diet low in fat with sufficient antioxidants can reduce the incidence of skin cancer in humans, Black 1998.

Range in Sun Sensitivity

For normal individuals without special skin conditions the ratio of the highest MED to the lowest MED usually has been found to be about 10 to 1 while some data indicates the ratio may be higher than 16 to 1. The range in MED's is for persons without special skin conditions such as vitiligo with a lack of melanin pigmentation in some areas of the skin.

The Fitzpatrick skin types based on skin color, sunburning and tanning characteristics are often used to estimate an individual's MED. Light colored hair or freckles are usually associated with skin types I or II and a correspondingly low MED, Azizi. Very dark blacks have the highest MED's. The UVB MED for Fitzpatrick type I through VI is listed as a range of 20 $mJ/cm^2$ to 200 $mJ/cm^2$, a ratio of 10 to 1 by Pathak. Damian found a ratio of slightly less, 7 to 1 for the highest MED to the lowest MED among 60 subjects in Australia.

A large ratio of the skin damage time for a very dark skinned black individual to the skin damage time for a light skinned individual was found to be 33 by Olson. However, Diffey found the perception of erythema for dark skin persons can be reduced by about a factor of two. Thus the factor of 33 found by Olson may represent only about a factor of 16 for the ratio of skin damage times between light skin subjects and dark skin subjects. Black skin transmits about 3% of ultraviolet light from a sunlamp while white skin transmits about 7 times as much, 22%. For white skin the stratum corneum transmits about 40% while the other layers transmit about 56% for an overall transmission of 22%. For black skin the stratum corneum transmits about 21% while the other layers transmit about 16% for an overall transmission of 3%, Kaidbey. The ratio of the transmission of the white skin and black skin samples measured by Kaidley thus is a little greater than 7 to 1.

Stratum corneum increases in thickness with exposure provide some additional protection but the primary protection is due to increased melanin pigmentation for sunlight exposure, Fitzpatrick 1986, Bech-Thomsen. Exposure to UVB light sources result in more protection from stratum corneum thickness than pigmentation increases. In contrast, exposure to UVA light sources result in the primarily protection being due to increased melanin pigmentation, Bech-Thompsen.

For those with highly sensitive skin, those at high risk of sunburn and skin cancer can be identified by physician examination with Wood's light and patient history as discussed by Fitzpatrick 1972. Important factors include light skin that does not tan well, red scalp hair, ephelides or freckles, sun induced lesions and sunburns lasting a week instead of fading in 2 to 3 days.

Skin Reflectance Measurements

Skin reflectance is a volume type effect and the term remittance is often used in place of reflectance. Reflectance usually refers to light reflected from a surface. The term remittance is often used rather than reflectance when the light is backscattered out of a volume. Since light penetrates a fraction of a millimeter into the skin and is scattered back out of the skin, remittance is the preferred term rather than reflectance. However, the term reflectance is often used rather than remittance. The pigments in the thin volume near the surface of the skin absorb the light in some wavelength ranges. Thus the reflected (or remitted light) is decreased in the wavelength ranges where pigments absorb the light.

For persons with darker skin the skin transmission is lower over a wide range of wavelengths. The range is from the ultraviolet B wavelengths near 300 nm to visible wavelengths and into the near infrared up to a wavelength just over 1100 nm, Anderson 1981, where the skin of both blacks and whites have essentially the same reflectance. Melanin, which provides protection at 300 nm absorbs over most of the range. However other pigments absorb in some parts of the range. To measure the melanin as an indicator of the sun sensitivity at 300 nm it is desirable to measure the reflectance in spectral regions where the melanin absorption is much larger than the absorption of other pigments. Measurements at 300 nm are undesirable as they require special ultraviolet equipment and the skin reflectance is low.

Wan shows the epidermis transmission to be lower for blacks than whites over the range of wavelengths from 300 nm to 800 nm. Thus a decreased reflectance at 610 nm associated with a decreased transmission at 610 nm indicates the 300 nm transmission will be decreased corresponding to a greater tolerance to sun exposure before sunburn occurs.

The primary pigments are melanin, bilirubin, carotene, deoxyhemoglobin and hemoglobin. Melanin is responsible for the variation from light skin to tan to dark black skin. Dark black skin has the highest concentrations of melanin and corresponding low sun sensitivity (high MED). Other pigments determine the other characteristic color differences between individuals and races. Reflectivity measurements have been used to estimate the melanin concentration. Measuring the melanin concentration has been of interest since it is strongly related to sun sensitivity. Wavelengths in regions where pigments other than melanin absorb are normally avoided to obtain as accurate as possible estimates of the melanin concentration. Both the red and blue/ultraviolet ends of the spectrum have been used for melanin measurements.

There are many bands where pigments other than melanin absorb light in the skin. High concentrations of bilirubin decrease the skin reflectivity over the range from 400 to 570 nm. At 450 nm the reflectivity decreases from roughly 36% at low concentrations to 18% for high concentrations, Hannemann. Feather, shows the absorption of deoxyhemoglobin to be high in the range of 520 to 610 nm. He selected wavelengths of 640 and 670 nm for reflectance measurements to determine the cutaneous melanin and 566 nm for the measurement of cutaneous hemoglobin. Jacquez shows another hemoglobin absorption in the reflectivity near 420 nm. Edwards and Duntley showed the pigment carotene results in a lowered skin reflectance near 482 nm.

Kuppenheim showed melanin absorbs over a wide range of wavelengths between 431 nm, his shortest wavelength of measurement to 1000 nm, his longest wavelength of measurement. Anderson 1982, in his FIGS. 6–11 shows heavily pigmented skin to have a low remittance (volume reflectance) compared to lightly pigmented skin in the spectral range between 600 nm and 700 nm. He showed that melanin does not significantly absorb above a wavelength of roughly 1150 nm. Anderson 1990, used ultraviolet remittance to determine a melanin index since the ultraviolet absorption is high providing ease of high accuracy measurements. He measured melanin absorption for wavelengths of 360 nm and longer as shown in his FIG. 6.

Jacquez, 1955 measured the spectral reflectance of the skin of the forearm of white males, males of Japanese descent and American blacks. The reflectance in the region 600 to 700 nm decreased with artificially induced erythema for the white males. The reflectance for the blacks in the 600 to 700 nm region was much lower than for the whites. His data shows three spectral regions with high reflectance that may be limited primarily by melanin pigmentation. One region is in the ultraviolet, 330 to 380 nm, one in the blue green region 450 nm to 520 nm and the third for red wavelengths longer than about 610 nm. The reflectance is higher for the longer wavelengths.

Anderson 1981 in his FIG. 8 shows melanin ultraviolet and visible molar extinction for melanin to be high compared to other pigments for wavelengths of 330 nm, 520 nm and 610 nm and longer.

Dwyer found reflectance differences for wavelengths of 400 nm and 420 nm to be effective in determining melanin density, however this region is difficult for visual grading of skin reflectance due to the low skin reflectance. Also, Dwyer compared wavelengths for predicting melanin density for light skin persons. For avoidance of changes in reflectance due to pigments other than melanin, the red wavelengths greater than 600 nm are useful. One reflectance spectrophotometer for determining the melanin level uses a wavelength of 655 nm, Thibodeau.

For those with moderate to low sun sensitivity, the melanin index was found to be useful in estimating the sun sensitivity in terms of the MED by Damian. The melanin index is based on the logarithm of the reciprocal of skin reflectivity. Measurements of skin reflectivity were related to the MED by Shono. Skin reflectance meters have been developed to measure the melanin index using monochromatic light emitting diodes with wavelengths of 640 nm and 670 nm Feather, 655 nm Thibodeau, 660 nm Lock-Anderson and 632 nm/ 905nm Damian. Takiwaki conducted experiments relative to relating the MED to MI and skin reflectivity measurements. The subjects were 16 healthy male Japanese aged 24 to 38 years at the University of Japan. The MED values ranged from 36 $mJ/cm^2$ to 72 $mJ/cm^2$ and the MI values ranged from 11.2 to 16.5. Takiwaki used the red, blue and green bands of a color video microscope to measure pigmentation and erythema.

Techniques such as skin fluorescence resulting from ultraviolet irradiation also can be used to determine the skin pigmentation, Leffell, however the equipment is relatively expensive.

Visual observations of skin reflectance have been used to grade pigmentation of ultraviolet-exposed mice by Hansen and by Nair. Nair used a four level grading which only provides gross differences. Hansen used a gray scale with many gray levels. A lamp was used to illuminate the mice and gray scale with purple light for the visual grading to determine the mouse skin reflectance.

Spectral remittance measurements of the skin between 620 nm and 720 nm provide an accurate means of determining the melanin content using a linear fit to the logarithm of the reciprocal of the remittance spectrum as verified by Kollias using subjects with vitiligo. Since the remittance over this wavelength range varied with the slope of the spectral remittance, a visual scale over the wavelengths greater than 600 nm should provide a reasonable estimate of the melanin content of the skin except in circumstances with skin hydration or skin disorders affecting the remittance.

A high skin reflectance is believed to be an even better indicator of photosensitivity than a low MED. This is due to the steep slope of degree of reddening with exposure associated with light colored skin with a high reflectance, Westerhof. The curve of reddening versus exposure is a better indicator of sun sensitivity than the MED since the MED represents only one point on the reddening curve. For steep slopes of the reddening curve associated with a low MED, only a slight overexposure can result in a painful burn.

Thick skin layers, both stratum corneum and epidermis, decrease the transmission both in the ultraviolet and longer wavelength visible regions. Part of this variation is expected to occur in the reflectance at visible wavelengths. Thus a decreased reflectance for visible wavelengths is expected to indicate a decreased ultraviolet transmission with associated sunlight exposure protection.

In summary, for visual reflectance measurements to estimate decreased sun sensitivity due to increased melanin pigmentation two spectral regions are available, one in the blue green region near 520 nm and one for red wavelengths greater than 610 nm. The skin reflectance for the red wavelengths is higher than for the blue green wavelengths.

Reflectance Measurement Devices

Many types of reflectometers use only narrow angle illumination and narrow angle detection which is suitable for specular reflectors but not for diffuse reflectors such as the skin. For wavelengths in the red region the light penetrates about a half millimeter into the skin and is scattered and emerges from the skin as diffuse wide angle light, Anderson, 1981. Outdoor illumination is a combination of narrow angle direct sun illumination and wide angle sky scattered illumination. Some reflectometers use integrating spheres for collecting wide angle diffusely reflected light but the illumination conditions differ from the combination of direct sunlight and skylight illumination.

The method and apparatus of Wulf (1998,1993, 1989) for determining an individual's ability to stand exposure to ultraviolet radiation is appropriate for measuring the skin reflectivity with a predetermined intensity source and a light detector. However, a lower cost apparatus or scale not requiring a predetermined intensity or special light source that is affordable to a large number of individuals is desirable.

The devices of Comment, MacFarland and DeWitt all require light sources and detectors for reflectance measurements with the associated cost and reliability problems limiting the number of persons who can afford the devices, replacement units and batteries.

Hansen used a scale for determining the reflectivity of mice skin, however, the low reflectivity for the purple wavelengths used required a light source with bright purple light. A scale that uses other wavelengths such as red light for which the skin reflectivity is higher is desirable so a filter rather than a special light source can be used.

All of the foregoing background references are hereby incorporated into the present application by this reference, as if fully set forth herein.

OBJECTS OF THE PRESENT INVENTION

An object of this invention is to provide apparatus and methods to enable individuals to be able to estimate both maximum sunlight exposure time to avoid sunburn and the minimum exposure time for previtamin D generation.

A further object is to estimate ultraviolet exposures so exposures can be reduced if necessary and maintained at a sufficiently low level over extended periods of time to reduce the risk of skin cancer.

Another object of the present invention is to propose an economical reflectance measurement apparatus with a specific adaptation for estimating the sun sensitivity of an individual's skin.

Another object is to provide methods and apparatus to determine minimum and maximum exposure for different areas of skin on the body.

Another object of the invention is to provide a method for individuals to determine how long their maximum sun exposure time is in comparison to values listed for an average type II individual.

Another object of the invention is to provide a method for individuals to determine how long their maximum sun exposure time without skin damage is increased as a tan is developed in the spring and summer.

A further object of the invention is to provide a method for individuals to ensure they obtain sufficient light exposure which is especially important for dark skin and older individuals who do not live in very bright environments or who are indoors most of the time.

Another object of the invention is to provide a device to compare surfaces under appropriate natural illumination rather than the artificial illumination used for many reflectometers.

Another object of the invention is to provide a device with low cost and long life so it is affordable for a large number of persons.

A still further object of the invention is to provide a low cost device for physician or medical personnel use to evaluate conditions such as jaundice that affect the spectral reflectivity of the skin when more expensive higher accuracy equipment is not available.

Consideration of the drawings and the descriptive text will show the objects are met by the apparatus and methods of this invention.

BRIEF SUMMARY OF THE INVENTION

The reflectance scale of the invention for use in meeting the objectives comprises an optical measuring device for comparing shades of a reference scale with the shade of an object and in particular an individual's skin viewed through a filter to determine the best match. When used for measuring skin, each shade of the reference scale can be used to estimate the sun sensitivity value (MED) for the viewed skin.

The method to estimate the exposure time when skin damage starts to occur and the exposure time necessary for desirable body functions such as previtamin D formation is to use the MED estimate along with enviromental characteristics from weather service data or tables of environment prediction tables from previously measured data or models.

The use of a filter for the reflectance scale apparatus has two advantages. First, restriction to wavelengths for which the reflectivity is determined primarily by melanin rather than other pigments provides a better measure of the melanin pigmentation which is a primary determinant of sun sensitivity. Second, the visual matching of reference reflecting areas to skin reflection is simplified if both are viewed in a single color.

Reflectivity measurements are of particular importance for use in estimating sun sensitivity since they are noninvasive. For light skin persons an important question is what is the best wavelength range to use to predict sun sensitivity. The melanin absorption which is strongly related to sun sensitivity is high in the ultraviolet, however, this spectral region is not suitable for a visual scale. The absorption is also high in for blue wavelengths but the low skin reflectivity tends to make measurements difficult without very bright illumination. The red end of the visual spectrum is frequently used to estimate the melanin concentration. Other pigments do not absorb in this region and the changes of reflectivity with the amount of melanin are sufficient for determination of the melanin level in the skin.

A high skin reflectance is believed to be an even better indicator of photosensitivity than a low MED. This is due to the steep slope of degree of reddening with exposure associated with light colored skin with a high reflectance.

Another advantage of the spectral reflectance scale is the skin and the scale can be viewed in outdoor sunlight which is a mixture of narrow angle incident direct radiation from the sun along with wide angle indirect radiation from the sky. Comparison of the skin with a mat diffusing surface gray scale provides a measurement under natural outdoor illumination conditions. The scale is best used for normal non-sunburned dry skin but not after exercise with excessive perspiration or after swimming with wet skin.

The reflectance technique of this invention has the potential for being an economical and effective method for determining the relative photosensitivity of individuals over the range from light skin to dark skin. The variation in sensitivity results from the primarily differing contents of melanin in the skin.

If a technique for determination of relative sun sensitivity is to be available to as many individuals as possible, a sufficiently low cost is essential. Even battery replacement cost can result in units not being used or thrown away.

This invention uses a filter for viewing the skin and scale to avoid the expense and possible eye hazards associated with a special blue/violet lamp as used in some research studies. The use of a filter along with the decreasing eye sensitivity at long wavelengths enables the restriction of viewed remittance to red wavelengths using a relatively low cost long wavelength pass filter.

Prior to use of the spectral reflectance scale for estimating solar radiation sensitivity, a calibration study of the measured MED versus skin reflectance measurement using the scale for many individuals with differing skin types should provide information for the MED prediction and the accuracy of the prediction.

To use the invention to measure skin reflectance the best match between the reference areas and the skin viewed through the filter is determined using sunlight illumination if possible. The melanin index then can be used with tables and daily solar radiation values to determine the exposure times to avoid overexposure or underexposure. To find the best match to the patches a convenient method is to first note which patch is close but definitely darker. Second a patch which is close but definitely lighter is noted. Third the patches in between these two are observed and the patch best matching the skin is selected.

The skin damage times and minimum exposure times for the type II individual can be determined using ultraviolet index predictions, solar ultraviolet radiation environment measurements or tables for particular locations, dates, sunlight and cloud conditions. Also color change cards and meters can be used to determine the erythemal ultraviolet radiation from the sun. The reflectance scale provides information for determining skin damage times and minimum exposure times for individuals other than skin type II individuals using the environmental data from the any of the various sources.

The reflectance scale methods and apparatus have the advantages of small size, low cost, long life and natural illumination in comparison to prior art devices. An important part of the low cost of the scale occurs since it can be used many times. Some other devices can only be used for only a few measurements and then another card must be purchased.

BRIEF DESCRIPTION OF THE SEVERAL VIEWS OF THE DRAWINGS

FIG. 6 (Table I) lists skin damage times and minimum exposure times for an individual with untanned type II skin having an MED of 21 mJ/cm$^2$.

FIG. 7 (Table II) lists patch reflectances and precalibration MED estimates for an example gray scale.

FIG. 8 (Table III) illustrates the determination of skin damage time in minutes using the MED of an individual and the National Weather Service solar ultraviolet index.

FIG. 8a (Table IIIa) lists the bright day skin damage times for Mobile Alabama.

FIG. 9 (Table IV) lists the clear day midday skin damage time by month for different latitudes.

FIG. 10 (Table V) lists the clear day exposure in MED's for 3% of the ambient exposure (typical for an office worker) for six months for different latitudes.

FIG. 11 (Table VI) lists the average day exposure in MED's (including effects such as clouds) for 3% of the ambient exposure (typical for an office worker) for January and October for different latitudes.

DESCRIPTION OF THE PREFERRED EMBODIMENTS OF THE INVENTION

Figure 1:
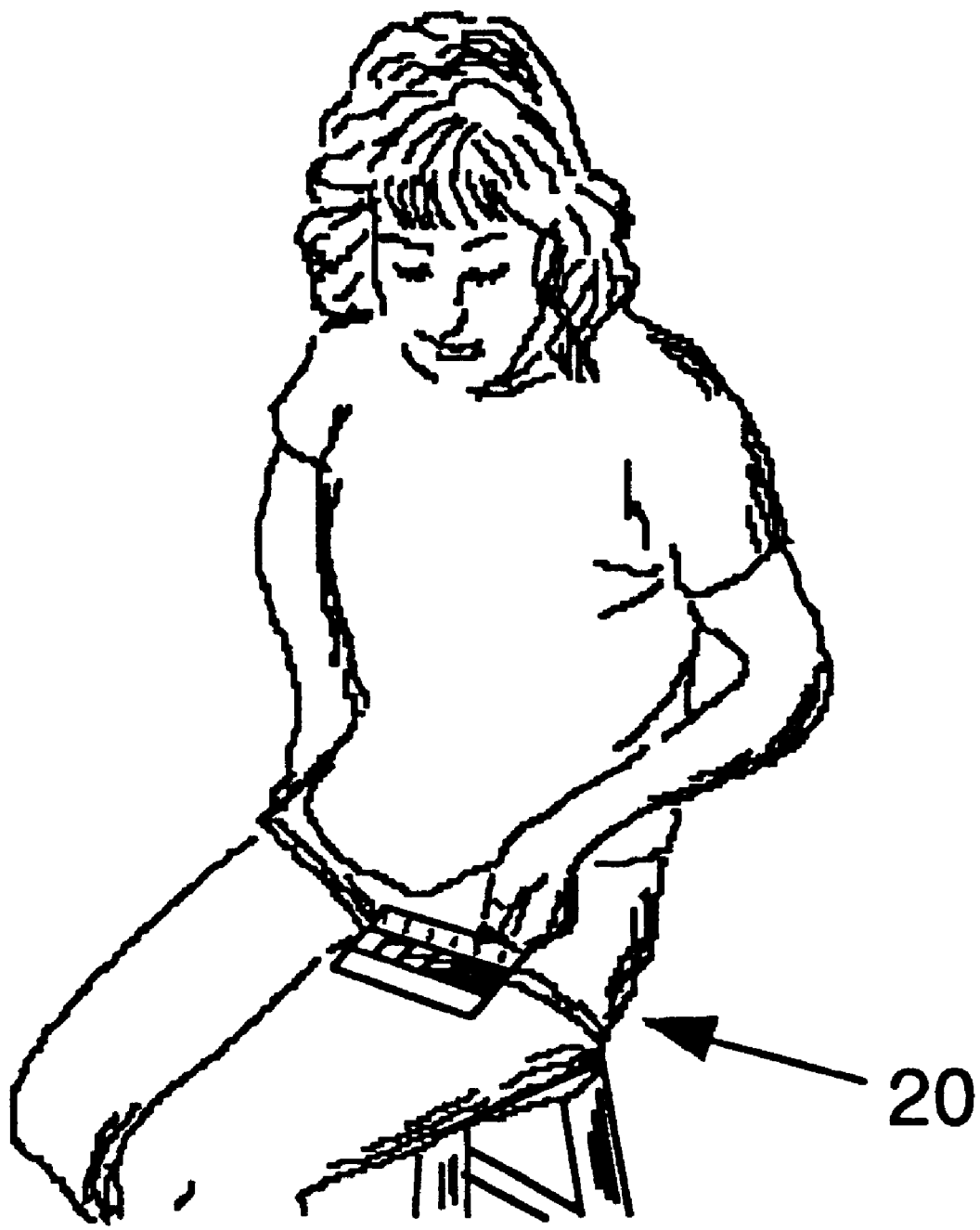
FIG. 1 is a view of a seated individual holding an embodiment of the spectral reflection scale on the upper leg to determine the melanin index of the skin under the scale.

An example use of the spectral reflectivity scale 20 apparatus for estimating the sun sensitivity (MED) of the skin viewed through the scale apparatus is illustrated in FIG. 1.

Figure 2:
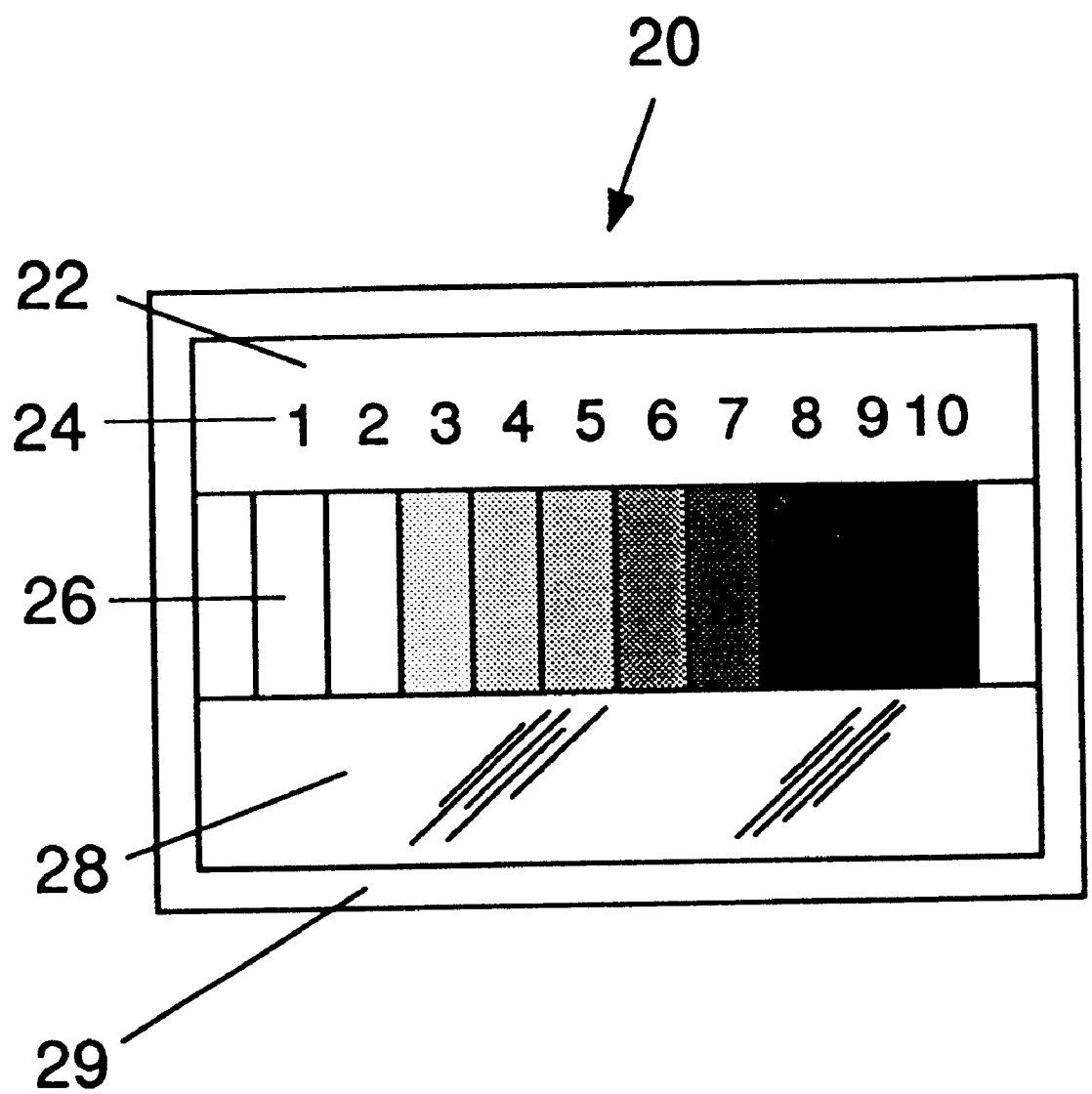
FIG. 2 is a top view of the preferred embodiment of the spectral reflectance index scale.
Figure 3:
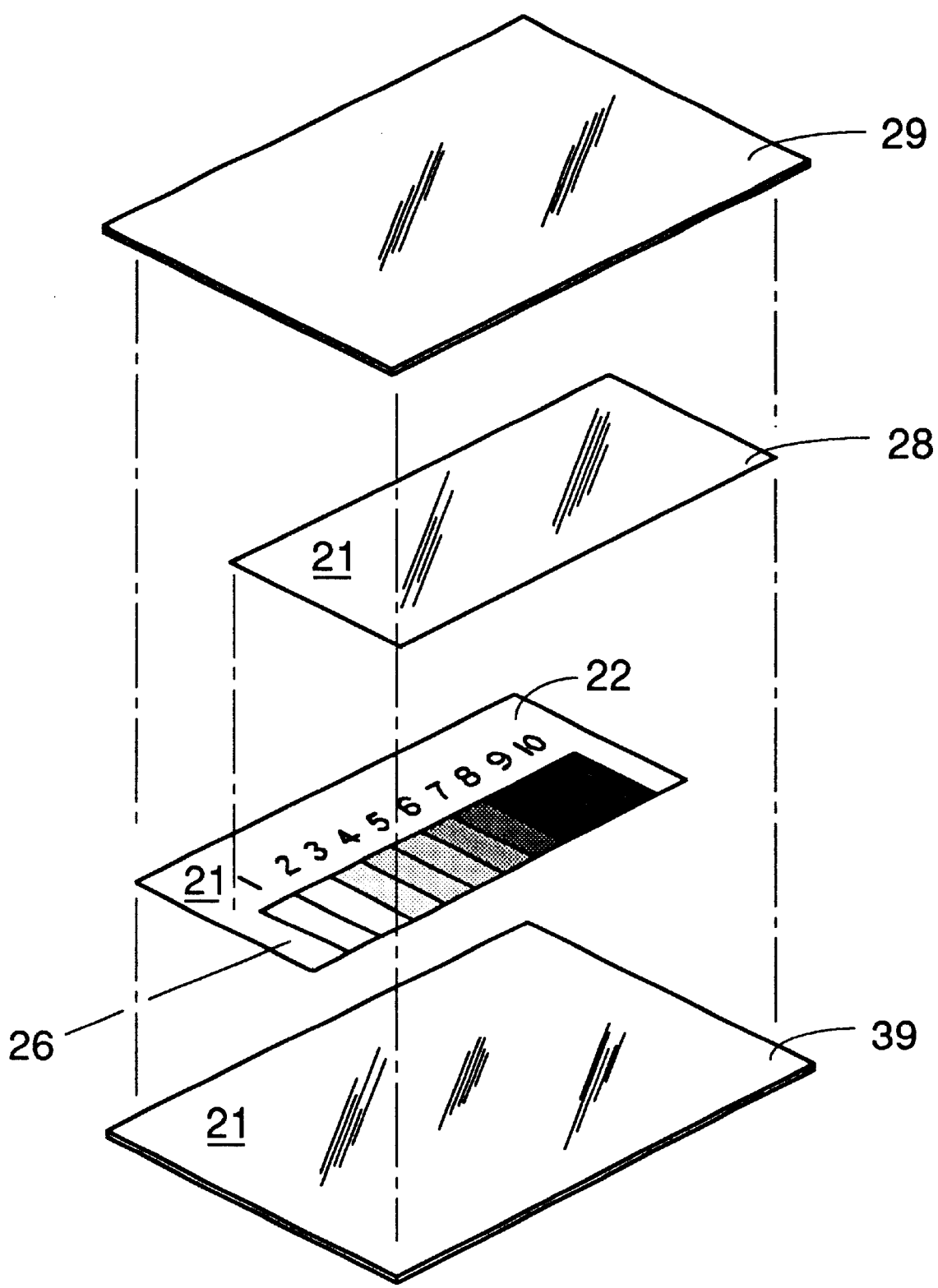
FIG. 3 is an exploded perspective view of the parts of an embodiment of the spectral reflectance scale prior to bonding them together.

Referring now to FIG. 2, the reflectivity scale 20 apparatus is comprised of a transparent spectral filter 28, a gray scale card 22 an upper transparent cover 29 and a lower transparent cover 39 identified in FIG. 3. The gray scale card 22 has gray scale patches 26 and identifiers 24 for the patches 26. The filter 28 extends over the gray scale patches 26. Thus both the gray scale and the object to be measured are viewed through the filter that is transparent to a portion of the visible light wavelengths (such as red light). An object or an individuals skin is viewed through the spectral filter through the area adjacent to the gray scale which is a rectangular opening in the gray scale card 22, referring now to FIG. 1 both the gray scale and skin of the upper leg of the individual are viewed through the same color filter facilitating identification of the best matching gray scale patch to the skin. By viewing other parts of the skin through the scale the melanin index can be determined for either tanned or untanned skin in other areas.

Referring now to FIG. 3 the exploded view of the parts prior to assembly, the spectral reflectivity scale is comprised of the transparent spectral filter 28, the gray scale card 22 with patches 26, the upper transparent protective cover 29, and the lower transparent protective cover 39 as illustrated. The parts shown in FIG. 3 can be joined by means of bonding with an adhesive 21 such as optical cement, laminated or held in a frame around the edges.

Typical materials for the filter include dye in plastic film such as Kodak Wratten™ No. 29. Typical materials for the gray scale are a photographic scale such as provided by Kodak™ in Cat 152 7654. Typical materials for the covers are plastics such as mylar and polished glass sheet as used for camera color filters. Typical adhesives include UV curing cement and index matching cement.

Figure 4:
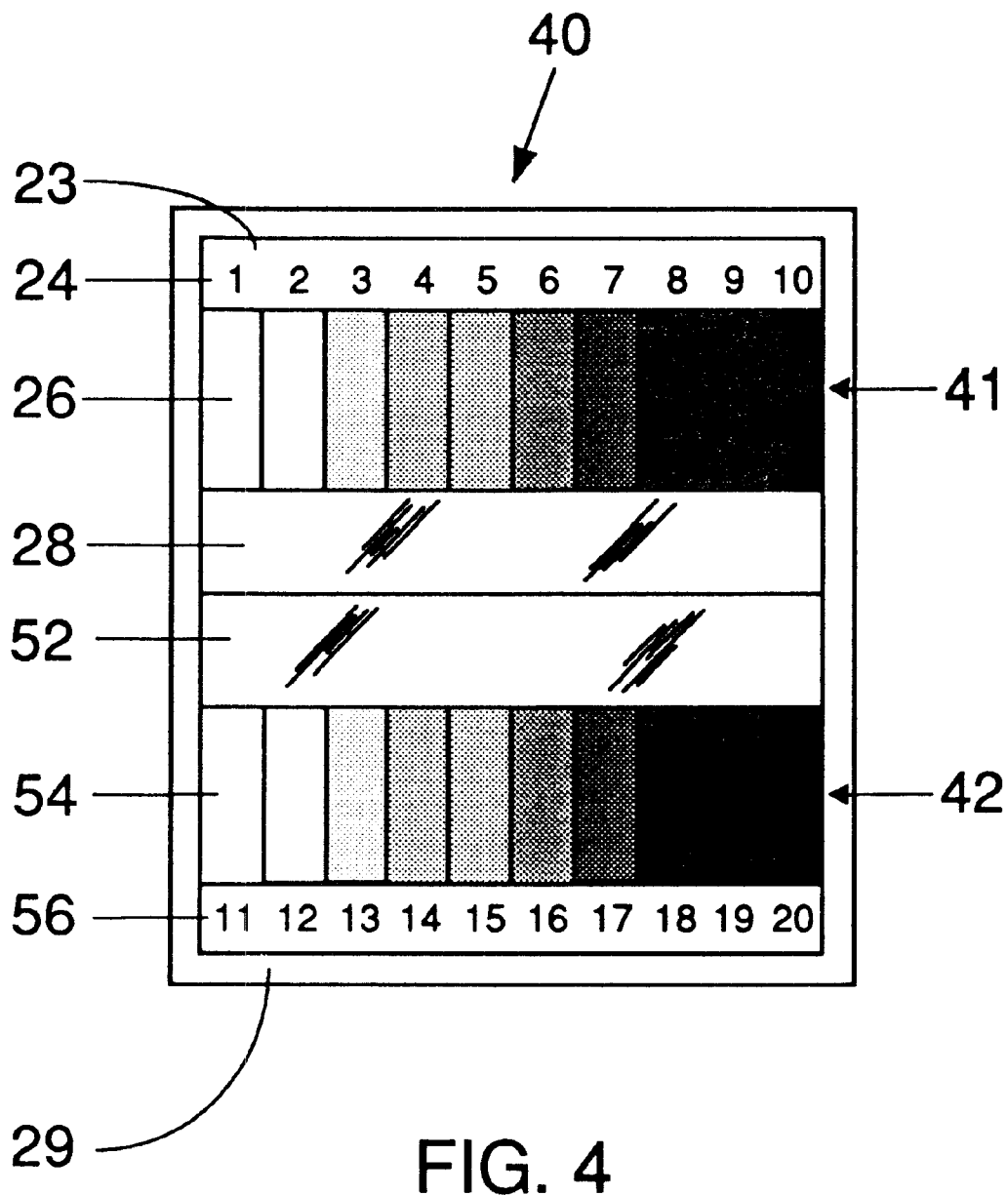
FIG. 4 is a top view of a dual scale embodiment of the spectral reflectance scale.
Figure 5:
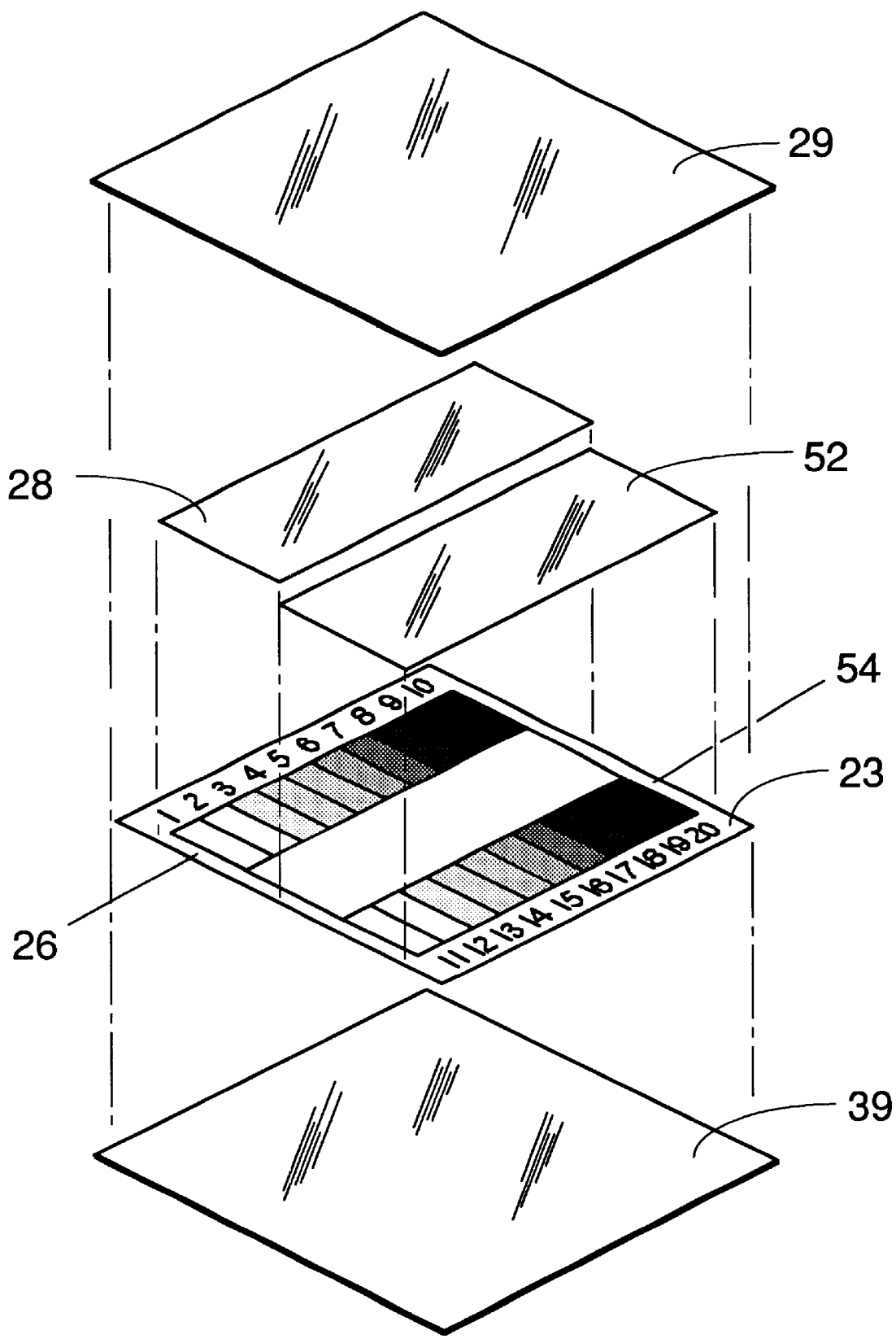
FIG. 5 is an exploded perspective view of the parts of the dual scale embodiment of the spectral reflectance scale with two filters prior to bonding the parts together.

Referring now to FIG. 4 and FIG. 5, in another embodiment 40, a gray scale card 23 with dual scales 41 and 42 under a protective cover 29 are used to obtain improved capability by use of two different spectral filters, 28 and 52. The patch identifiers 24 and 56 for the patches 26 and 54 are used with tables listing the reflectivity associated with each patch to determine the skin reflectivity in the spectral wavelength bands of the filters 28 and 52. One filter 28 can be used to measure melanin pigmentation and the other filter 52 can be used to measure erythema in conjunction with filter 28. Other filter pairs can be used to estimate hemoglobin, bilirubin or other conditions affecting skin reflectance.

In FIG. 5, an exploded view of the dual scale parts prior to joining them together the parts include the gray scale card 23, filters 28, 52 and protective covers 29,39. The filter 28 is placed over the patches 26 numbered 1 through 10 and part of the rectangular opening 58 between the two sets of patches. The other filter 52 is placed over the set of patches 54 numbered 11 through 20 and the remainder of the opening 58 not covered by filter 28. An upper protective cover 29 and a lower protective cover 39 enclose the plastic filters 28, 52 and printed or photographic gray scales 41, 42. The gray scale patches 26, 54 have identifier numbers 24, 56.

Figure 5A:
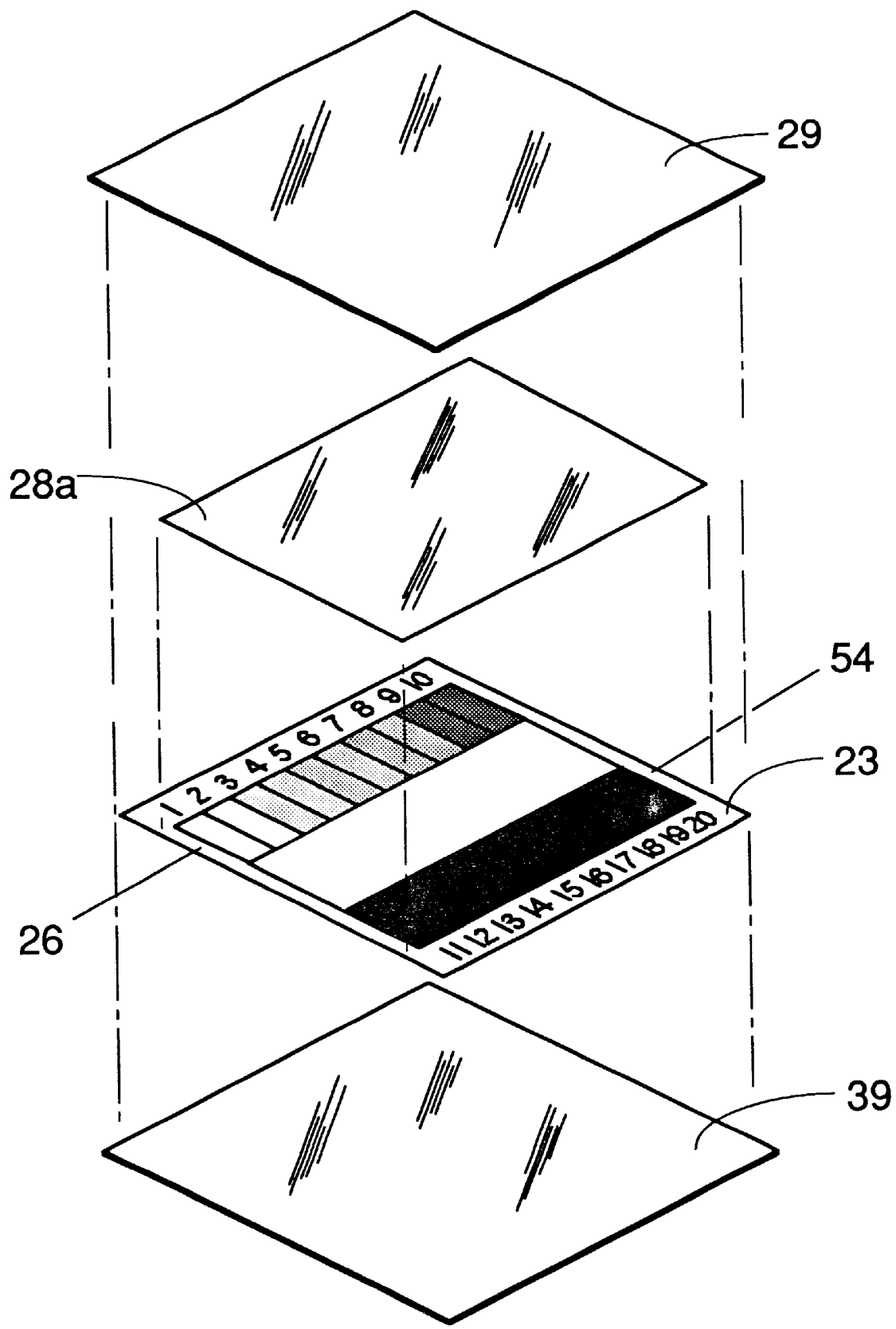
FIG. 5a is an exploded perspective view of the parts of the dual scale embodiment of the spectral reflectance scale with a single filter prior to bonding the parts together.

Referring now to FIG. 5a, a further embodiment uses only one spectral filter type 28a for filters 28 and 52 in FIG. 5 and extends over both sets of patches 26a and 54a. An increased number of gray scale patches 26a and 54a for the gray scale card 23a can be used in a compact arrangement in comparison to a card with all the patches 26a and 54a in a single row. A large number of patches offers increased accuracy of reflectivity measurement. As an example the patches 1 through 10 in FIG. 5a can be a lighter set of patches while the darker set of patches can be 11 through 20 rather than each set ranging from light to dark as in FIG. 5. The upper protective cover 29 and the lower protective cover 39 in FIG. 5a along with the filter 28a and the gray scale card 23a are bonded together using an adhesive 21 a in various locations as illustrated prior to use of the device.

Table I (FIG. 6) lists the skin damage times and minimum exposure times for an individual with type II skin having an MED of 21 mJ/cm$^2$. The skin damage time values in seconds were determined using the ratio of the MED in mJ/m$^2$ to the product of the UV index and 25 mW/m$^2$. The skin damage times in seconds were then converted to skin damage times in minutes and the results are listed in Table I. The minimum exposure times were determined using an average exposure of 55 MED/year (0.15 MED/day) recommended in the World Health Organization publication on ultraviolet radiation. In a preferred embodiment a card is provided with the data in Table I (FIG. 6) as part of the package.

For some functions such as previtamin D formation in the skin by ultraviolet B radiation a much lower value than 0.15 MED/day is sufficient if a large fraction of the body is irradiated such as when wearing a swimsuit. In cold weather outdoors only the face and hands are usually exposed and a higher value such as 0.15 MED is necessary.

Table I is useful for the many light skinned individuals with an MED near 21 mJ/cm$^2$. However, the problem for others is to estimate their MED relative to the type II individual. This is the subject of this invention and is accomplished using the reflectivity scale along with tables relative to sun sensitivity.

Skin Damage Exposure Time

To use the apparatus to determine the skin damage, time one first determines the best matching scale patch for the lightest skin to be exposed as shown in FIG. 1 if the upper leg is the lightest area. Second, a table similar to Table II (FIG. 7) is used to find the corresponding MED. Experimental measurements of MED on many subjects will be necessary to verify MED values for Table II. If the lightest skin corresponds to patch 2, then the table indicates the precalibration example MED is 20 mJ/cm$^2$. In a preferred embodiment a card is provided including the data in Table II (FIG. 7) as part of the package.

The precalibration example MED values in Table II were selected by observing the matching patches for light skin persons are often for patch 2 and light skin persons commonly have an MED near 20 mJ/cm$^2$. A very dark skin persons matched patch 11 and very dark skin persons have MED's near 200 mJ/cm$^2$. For patches 2 through 12 the log reciprocal reflectivity is linearly related to the MED values.

The determination of skin damage time is especially important for those with high sensitivity skin. The National Weather Service provides ultraviolet index (UVI) predictions for some local areas and the current day. By way of example for a summer day in a low latitude city, assume the UVI value is found to be 8. A matrix table similar to that in FIG. 8 (Table III) is used with the MED value and the ultraviolet index to look up the estimated burn time. The values in the table in Table III were determined using the ultraviolet index unit of 25 milliwatts/square meter value for the erythemally weighted dose rate. As an example if the MED is 20 mj/cm$^2$ for an individual in a city where the predicted noon time UVI is 8 then the skin damage time near noon in minutes as listed in Table III is 17 minutes. In a preferred embodiment a card is provided with the data in Table III (FIG. 8) as part of the package.

The National Weather Service tabulates the maximum UV index by month for 58 cities and the values for 1997 are listed in their website. The MED and the maximum UV index can be used to evaluate a typical skin damage time by month for the various cities as illustrated for Mobile Alabama in FIG. 8a (Table IIIa). An individual with an MED of 40 mJ/cm$^2$ would have had a shortest skin damage time for the month of August of 30 minutes in 1997. Since the times do not change greatly from year to year the time of 30 minutes can be used in planning outdoor activities, the use of protective clothing, headwear and sunscreen lotion.

The patch reflectivities in FIG. 7 corresponding to the MED values are rough estimates using reflectivity data and MED data for whites and blacks. Calibration data for a large number of individuals will be necessary to establish the reflectivities corresponding to the MED values.

An advantage of the reflectance scale is it can be used to estimate the MED for the lightest skin to be exposed. For hiking this might be the arms and lower legs if long shorts are worn. For swimming, the lightest colored skin not covered by the bathing suit can be measured using the reflectance scale. The back, chest, shoulders and upper legs are common areas for sunburns depending on the body positions relative to sunlight during an exposure.

By use of the reflectance scale of this invention the determination of MED from skin color should be simplified in comparison to the subjective judgment of differences such as brown versus dark brown.

Once the MED has been estimated the skin damage time can be determined using tables similar to Table IV (FIG. 9). Table IV is an example of skin damage times for different months and latitudes using an example MED of 20 mJ/cm$^2$. For an MED of 40 mJ/cm$^2$ the skin damage times are twice the values in the table. For example for a latitude of 35 degrees and the month of June the burn time for an MED of 20 mJ/cm$^2$ is 18 minutes. For the same month and latitude a darker skin person with an MED of 40 mJ/cm$^2$ has a skin damage time of 36 minutes. For areas at high elevations the increased ultraviolet transmission of the decreased path length through the atmosphere will result in shorter skin damage times, about 6%/km.

The use of sunscreen can extend the skin damage time. The use of a screen with an effective SPF of 10 increases the skin damage time by a factor of ten. A sunscreen labeled with an SPF of 20 can have an effective SPF of only 10 since the sunscreen thickness on the skin is often thinner than the thickness use for evaluating the sunscreen.

One of the comments on the National Weather Service ultraviolet index values is they do not vary greatly with time for clear days when the skin damage time is of greatest interest. For this reason tables such as Table IV are convenient as a guide in planning outdoor activities and the use of sun protection techniques rather than waiting for UVI predictions for the day of the activities. In a preferred embodiment a card is provided with the data in Table IV (FIG. 9) as part of the package.

MED values listed in research studies vary from one study to another due to the variation in equipment, differences in subjects from country to country, the methods for analyzing the data and the limited number of test subjects. There are several weighting factors, WHO page 61, used to determine the MED resulting in variations in MED's reported by different studies. For this reason it is important to conduct preliminary studies with the reflectance scale to determine the relation of MED and skin damage time to the best matching patch of the scale. When first using the scale it was evident optical density steps of less than 0.1 may be useful in skin grading for some of those with relatively light skin since individuals tended to interpolate between patches. For very dark skinned blacks a scale without a red filter may be suitable since the reflectivity is low and the black scale matches the skin color fairly well. Adjustment of the scale based on experimental data for racial groups or individuals in particular countries should provide better estimation of the MED corresponding to patches of the scale.

It is important to recognize the skin damage time is the maximum exposure time is for avoiding sunburn on a single day. Many exposures less than the maximum exposure time may result in skin cancer. Thus the maximum exposure time is not a safe time relative to developing skin cancer if the exposures are repeated for a large number of days over a long period of time.

Minimum Sun Exposure Time (Avoidance of Insufficient Sunlight Exposure)

To determine the minimum sun exposure time for dark skinned persons in the winter months the UV index is of limited usefulness. The time necessary can be most of the day and the UV index is only relevant to the period near solar noon. Environmental models and the type of UVB dose data published by the Solar Light Company™ for Philadelphia in their website is appropriate for determining the minimum outdoor exposure time when the exposure time extends over much of the day.

The environmental model for the clear sky daily solar radiation for each month at different latitudes can be used to estimate the average daily erythemal exposure. For office workers the 3% exposure to ambient environment percentage combined with values from the clear day environment model were used to calculate the values for the average daily exposure in MED's for individuals with MED's as listed for the latitudes between 0 and 50 degrees in Table V (FIG. 10). The exposures are for low elevations areas and for areas at high elevations the exposures in MED's will be increased by 6%/km or more.

Table V is useful in determining the periods when sunlight exposure is less than the WHO recommended level of 55 MED/year (0.15 MED/day). For example, an office worker with light skin with an MED of 20 mJ/cm$^2$ living at a latitude of 50 degrees will on the average experience an exposure of 0.06 MED/day during the month of December. The 0.06 MED exposure is less than half the recommended average exposure of 0.15 MED. Knowing the exposure to be low the office worker might try taking a half hour walk outside at lunch time during December. The added exposure can be evaluated using the WHO value (Table 3.2 on page 22) of 8 mW/m² for the noontime erythemally effective UVB irradiance at 50 degrees latitude (8 mW/m²*1800 seconds*0.10 efficiency/(20 mJ/cm²*10,000 cm²/m²)) or 0.01 MED. The efficiency is 10% for the ratio for outdoor exposure to the ambient ultraviolet radiation environment. Thus the daily exposure is increased from 0.06 to 0.07 MED which is still significantly less than the recommended exposure of 0.15 MED. Thus other methods are necessary to obtain an exposure close to the recommended exposure.

The uniformity of the light environment from month to month in low latitude areas in comparison to high latitude areas is shown by the values in Table V. For a dark skin person with an MED of 160 mJ/cm² living near zero degrees latitude the exposure for the six months listed ranges from 0.15 to 0.19 MED/day close to the WHO recommended exposure of 55 MED/year (0.15 MED/day). At 50 degrees north a light skin person with an MED of 20 mJ/cm² has a very low average exposure of 0.06 MED/day in December and an exposure of 1.02 MED/day for a clear day in June. The large change is a stressful environment at the high latitude in comparison with the much smaller variations at low latitudes.

For dark skinned office workers with an MED of 80 MJ/cm² the average exposure at latitudes above 30 degrees is less than 0.15 MED for the months of November through January as listed in Table V. Additional exposure from lamps or other means is necessary to obtain the recommended daily exposure level.

The range of 160 mJ/cm² to 20 mJ/cm² in Table V is a ratio of 8 to 1. Thus, overall the underexposure problem for dark skin individuals may be even more severe than illustrated by Table V. In a preferred embodiment a card is provided including the data in Table V (FIG. 10) as part of the package.

The environmental model for global ultraviolet radiation including the effects of clouds and surface elevation was used to calculate the values in Table VI (FIG. 11). The low average daily exposures for dark skin persons with an MED of 80 mJ/cm² for the months of January and October at high latitudes are illustrated by the values for the exposures less than 0.15 MED in Table VI (FIG. 11) using this model. The exposure at 40 degrees latitude for the month of January for an office worker with an MED of 80 mJ/cm² for a clear day is 0.06 MED as listed in Table V. The corresponding value for an average day including the effects of clouds and other factors is 0.02 MED as listed in Table VI. In both cases the exposure is considerably below the recommended average value of 0.15 MED/day. In a preferred embodiment a card is provided with the data in Table VI (FIG. 11) as part of the package.

Reduction of Skin Cancer Risk

As demonstrated by animal tests many exposures near the burn limit result in a large fraction of animals with skin cancer. Skin cancer statistics for different geographical areas and persons of different ages indicate the accumulated dose increases the risk of cancer. By maintaining a low average dose over long periods of time the risk of skin cancer can be reduced.

Keeping the exposure below the sunburn limit is not effective in keeping the skin cancer risk low if there are many exposures near the skin damage limit. Since the accumulated dose is important, if one is close to the skin damage limit only for rare occasions then there will not be a significant increase in skin cancer risk. However, if one frequently has high doses near the skin damage limit the risk of skin cancer can be significantly increased.

As an example of a skin cancer risk reduction method, if an outdoor worker uses the filter reflectance scale to estimate his MED and finds his daily exposures using the local environment tables to be close to 1 MED/day then he needs to use added protection if he wishes to keep the risk of skin cancer low. By using clothing, head covering and sunscreen to reduce the exposure to about 0.15 MED/day he should be receiving sufficient sunlight for previtamin D formation and at the same time reduce his risk of developing skin cancer later in life or delay the occurrence.

If there was a large accumulated dose in childhood, which is very common, then skin cancers may still develop at some age. However, adding the protection after childhood tends to delay the occurrence of skin cancer to older ages than without the use of protection techniques.

Reflectance Scale Characteristics and Use

The number of reflectance patches determines the accuracy of the reflectance scale. The high contrast sensitivity of the eye using bright outdoor illumination enables precise matching of the patches to the skin as viewed through the filter. For very dark blacks use of the reflectance scale without the filter may be possible since other pigments have very small effect compared with the melanin.

Observation of several individuals using the reflectance scale resulted in the lightest having a reflective greater than 71% and the darkest individual had a reflectivity of about 7%. Table II illustrates typical patch reflectances for determination of skin reflectance.

Figure 12:
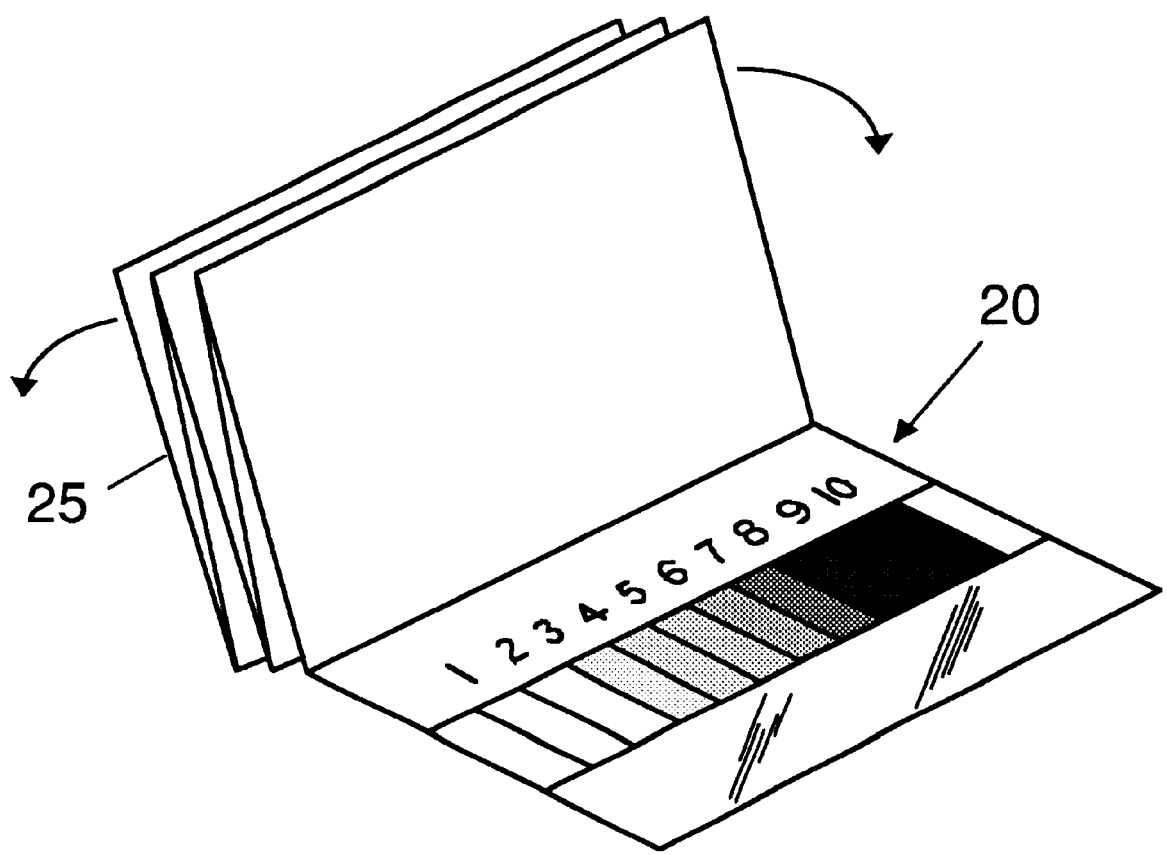
FIG. 12 is a perspective view of the reflectance scale with fold out cards for tables.

For dark skin persons the primary advantage of the reflectance scale is likely to be in finding how much the exposure should be increased in the fall and winter to obtain sufficient sunlight for previtamin D generation. FIG. 12 illustrates an embodiment with fold out cards 25 attached to the reflectance scale 20 so tables on the fold out cards can be attached to the scale 20. For simplicity of use the information on the cards can be provided for particular areas such as metropolitan areas.

The apparatus and methods of this invention make it possible for an individual to estimate his or her sun sensitivity relative to an average type II individual, the difference in sun sensitivity for different parts of the skin and the variation in sensitivity with time due to tanning. The determination of the variation in sun sensitivity due to medication, chemical exposure, environmental substances and medical conditions such as systemic lupus erythematosus (SLE) is not included in this invention and requires a technique such as direct measurement of the MED or knowledge from previous experiments.

The apparatus and methods of this invention are useful for an individual to estimate his or her sensitivity relative to an average type II skin type.

For many of the large number of persons without unusual skin conditions the reflectance scale invention should enable exposure adjustment to obtain a balanced, moderate and sufficient exposure to increase the probability for improved health.

REFERENCES CITED

U.S. Patent Documents

| | | | |
|---|---|---|---|
| 4,846,184 | 7/89 | Skin reflectance measuring apparatus, Comment | 128/633 |
| 4,894,547 | 1/90 | Opt. method and apparatus for measuring pigmentation in skin, Leffell | 250/461.2 |
| 5,671,735 | 9/97 | Method and apparatus for detecting and measuring conditions affecting color, MacFarland | 128/633 |
| 4,423,736 | 10/81 | Method for evaluation of erythema utilizing skin reflectance measurements, DeWitt | 128/633 |
| 4,882,598 | 11/89 | Method and an apparatus for determining an individual's ability to stand exposure to UV radiation, Wulf | 250/338.1; 250/372 |

International Patent Documents

| | | | | |
|---|---|---|---|---|
| EP 629124 | 8/98 | Skin UV radiation sensitivity measuring- | Wulf | A61-005/103 |
| WO 9316635 | 9/93 | Skin UV radiation sensitivity measuring- | Wulf | A61-005/103 |
| DE 69319585 | 8/98 | Skin UV radiation sensitivity measuring- | Wulf | A61-005/103 |

Other Publications

Anderson, R. Roy and John A. Parrish: The optics of the skin. Jour. Invest. Dermatol. 77:13–19, 1981.

Anderson, R. Roy and John A. Parrish: Optical properties of human skin. In: The Science of Photomedicine Ed by James D. Regan and John A. Parish. Plenum Press, New York 1982.

Azizi, E., A. Lusky, A. P. Kushelevsky and M. Schewach-Millet: Skin type, hair color, and freckles are predictors of decreased minimal ultraviolet radiation dose. J. of Am . Acad. of Dermatol. 19:32–38;1988.

Bech-Thomsen, N., H. C. Wulf: Photoprotection due to pigmentation and epidermal thickness after repeated exposure to ultraviolet light and psoralen plus ultraviolet A therapy. Photodermatol Photoimmuno & Photomed 11:213–218;1995.

Black, Homer S., Wanda A. Lenger, Janette Gerguis, and John I. Thomby: Relation of antioxidants and level of dietary lipid to epidermal lipid peroxidation and ultraviolet carcinogenesis. Cancer Res. 45:6254–6259; 1985.

Black, Homer S., Goodluck Okotie-Eboh, Janette Gerguis, Julie I. Urban and John I Thomby: Dietary fat modulates immunoresponsiveness in UV-irradiated mice. Photochemistry and Photobiology 62;964–969;1995.

Black, Homer S.: Influence of dietary factors on actinically-induced skin cancer. Mutation Res. 422:185–190;1998.

Blum, Harold F.: Carcinogenesis by ultraviolet light. Princeton Univ. Press. Princeton N.J. 1959. page 195.

Chen, Tai C.: Photobiology of vitamin D, p30. In Vitamin D ed by Michael F. Holick. Humana Press, Totowa, N. J. 1999.

Damian, D. L., G. M. Halliday and R.StC. Bametson: Prediction of the minimal erythemal dose with a reflectance melanin meter. Br. J. of Dermatol. 136:714–718:1997.

Diffey, B. L. and J. Robson: The influence of pigmentation and illumination on the perception of erythema. Photodetermatol Photoimmunol Photomed 9:45–47;1992.

Dwyer, Terence, H. Konrad Muller, Leigh Blizard, Rosie Ashbolt and Geoffrey Phillips: The use of spectrophotometry to estimate melanin density in Caucasians. Cancer Epidemiology, Biomarkers & Prevention 7,203–206;1998.

Hansen, A. B., N. Bech Thomsen, H. C. Wulf: In vivo estimation of pigmentation in ultraviolet-exposed hairless mice. Photodermatol. Photoimmuno. Photomed. 11;14–17;1995.

Leach, J. F., V. E. McLeod, A. R. Pingstone, A. Davis and G. H. W. Deane: Measurement of the ultraviolet doses received by office workers. Clin and Exp Dermatol 3:77–79;1978.

Edwards, E. A. and S. Q. Duntley: The pigments and color of living human skin. Am. J. Anat. 65:1–33;1939.

Epstein, John H.: Xeroderma pigmentosum and UVL carcinogenesis. Page 299–315 in Sunlight and Man edited by Thomas B. Fitzpatrick. Univ. of Tokyo Press, 1972.

Feather, J. W., D. J. Ellis and G. Leslie: A portable reflectometer for the rapid quantification of cutaneous haemoglobin and melanin. Phys. Med. Biol. 33: 711–722, 1988.

Fitzpatrick, Thomas B., Madhu A. Pathak and John A. Parrish: Protection of the human skin against the effects of sunburn ultraviolet (290–320 nm). In Sunlight and Man edited by Thomas B. Fitzpatrick. Univ. of Tokyo Press, 1972.

Fitzpatrick, Thomas B.: Ultraviolet-induced pigmentation changes: benefits and hazards. Curr Probl Derm 15:25–38;1986.

Garland, Cedric F., Frank C. Garland, and Edward D. Gorham: Epidemiology of cancer risk and vitamin D. In: Vitamin D, Ed. Michael F. Holick, Humana Press, Totowa, New Jersey, 1999.

Geller, Alan C., Drusilla Hufford et al.: Evaluation of the ultraviolet index: media reactions and public response. Jour of the Am Acad of Dermatol. 37:935–941;1997.

Hannemann, R. E., D. P. DeWitt and J. F. Wiechel: Neonatal serum bilirubin from skin reflectance. Pediat. Res. 12:207–210;1978.

Hansen, A. B., N. Bech-Thomsen and H. C. Wulf: In vivo estimation of pigmentation in ultraviolet-exposed hairless mice. Photomed Photoimmunol Photomed 11:14–17;1995.

Holick, Michael F.: The photobiology of vitamin D and its consequences for humans. In: The medical and biological effects of light. Annals of the New York Academy of Sciences vol 453, p1–13. 1985.

Jacquez, J. A., Hans F. Kuppenheim, J. A. Dimitroff, W. McKeehan and J. Huss: Spectral reflectance of human skin in the region 235–700 m$\mu$. J. Appl. Physiol. 8:212–214;1955.

Jacquez, J. A. and Hans F. Kuppenheim: Spectral reflectance of human skin in the region 235–1000 m$\mu$. J. Appl. Physiol. 8:297–299;1956.

Kaidbey, Kays H., Patricia Poh Agin, Robert M. Sayre and Albert M. Kligman: Photoprotection by melanin-a comparison of black and Caucasian skin. J Am Acad Dermatol 1:249–260;1979.

Kime, Z. R.: Sunlight. World Health Publications, Penryn, Calif. (1980).

Kollias, N. and Ali Baqer: On the assessment of melanin in human skin in vivo. Photochem and Photobio 43:49–54;1986.

Kuppenheim, Hans F. and R. R. Heer, Jr.: Spectral reflectance of white and Negro skin between 440 and 1000 m$\mu$. J. Appl. Physiol. 4:800–806;1952.

Lock-Anderson, J., N. D. Knudstorp and H. C. Wulf: Facultative skin pigmentation in Caucasians. Brit. J. Dermatol. 138:826–832;1998.

Long, C. S., A. J. Miller, Hai-Tien Lee, Jeannette D. Wild, R. C. Przywarty, and Drusilla Hufford: Ultraviolet index forecasts issued by the National Weather Service. Bulletin of the American Meteorological Society, 77:729–748;1996.

Madronich, S.: p 32 in UV-B Radiation and Ozone Depletion, Ed. by M. Tevini. Lewis Publishers, Boca Raton, 1993.

Mosley, H., R. M. Mackie and J. Ferguson: The suitability of SunCheck® patches and Tanscan® cards for monitoring the sunburning effectiveness of sunlight. Br. J. Dermatol. 128:75–78;1993.

Nair, Xina and Kenneth M. Tramposch: UVB-induced pigmentation in hairless mice as an in vivo assay for topical skin-depigmenting activity. Skin Pharmacol 2:187–197;1989.

Olson, Robert L., James Gaylor, and Mark Allen Everett: Skin color, melanin and erythema. Arch. Dermatol. 108:541–544;1973.

Pathak, Madhu A.: Photoprotective role of melanin (eumelanin) in human skin, p 337–344I in: Light in biology and medicine, vol 1,ed. by Ron H. Douglas, Johan Moan and F. Dall'Acqua. Plenumi Press, New York, 1988.

Sabziparvar, Ali A., Keith P. Shine and Piers M. de F. Foster: A model-derived global climatology of UV irradiation at the earth's surface. Photochem. and Photobio. 69: 193–202;1999.

Satoh, Y., T. Irimajiri, S Okawara, K. Shimao and M. Seiji: A newly designed monochromator and action spectra of various photodermatoses. Page 575–590 in Sunlight and Man edited by Thomas B. Fitzpatrick. Univ. of Tokyo Press, 1972.

Sheehan, John M., Christopher S. Potten and Antony R. Young: Tanning in human skin types II and III offers modest photoprotection against erythema. Photochem. and Photobio. 68(4):588–592;1998.

Shigenaga, M. K. and Ames, B. N.: Oxidants and mitogenesis as causes of mutation and cancer: The influences of diet. In: Antimutagenesis and Anticarcinogenesis Mechanisms III. Ed by G. Bronzetti, H. Hayatsu, et al. Plenum Press, New York. 1993. p 419–436.

Shono, S., M. Imura, M. Ota, S. Ono, and K. Toda: The relationship of skin color, UVB-induced erythema, and melanogenesis. Jour. Invest. Dermatol. 84:265–267,1985.

Takiwaki, Hirotsugu, Shiro Shirai, Hiroaki Kohno, Hemi Soh, and Seiji Arase: The degrees of UVB-induced erythema and pigmentation correlate linearly and are reduced in a parallel manner by topical anti-inflammatory agents. Jour. Investigative Dermatol. 1994:103,642–646.

Thibodeau, E. A., and J. A. Ambrosio: Measurement of lip and skin pigmentation using reflectance spectrophotometry. Eur. J. Oral Sci. 105:373–375;1997.

Urbach, F.: Phototoxic skin reaction to UVR-Is "sunburn" a "burn"? Photodermatol Photoimmuno Photomed 12:219–221;1996.

Wan, San, K. F. Jaenicke and John A. Parrish: Comparison of the erythemogenic effectiveness of ultraviolet-B (290–320 nm) and ultraviolet-A (320–400 nm) radiation by skin reflectance. Photochem and Photobio. 37:547–552;1983.

What is claimed is:

1. A scale card assembly comprising, in sequence:
   (a) an upper transmitting protective cover;
   (b) a transmitting spectral filter;
   (c) at least one gray scale card containing a plurality of patches of differing reflection areas;
   (d) a lower protective cover; and
   (e) means to join said filter, said gray sale card, and said protective covers;
   whereby said gray scale card may be observed through said upper transparent protective cover and said transmitting spectral filter.

2. An assembly according to claim 1, wherein said gray scale card includes at least two scales with said spectral filter extending over both scales.

3. An assembly according to claim 2, wherein said transmitting spectral filter includes at least a pair of spectral filters.

4. An assembly according to claim 3, wherein said at least a pair of spectral filters are aligned but spaced apart.

5. An assembly according to claim 2, wherein said transmitting spectral filter includes a single spectral filter extending over said at least two scales.

6. An assembly according to claim 1, including at least one card containing exposure data.

7. An assembly according to claim 6, including more than one card containing melanin index data.

8. An assembly according to claim 7, including a plot of solar UV index and MED data to determine skin damage times.

* * * * *